(12) United States Patent
Ritland

(10) Patent No.: US 7,166,073 B2
(45) Date of Patent: Jan. 23, 2007

(54) METHOD AND DEVICE FOR MICROSURGICAL INTERMUSCULAR SPINAL SURGERY

(75) Inventor: Stephen Ritland, 1150 N. San Francisco St., Flagstaff, AZ (US) 86001

(73) Assignee: Stephen Ritland, Flagstaff, AZ (US)

( * ) Notice: Subject to any disclaimer, the term of this patent is extended or adjusted under 35 U.S.C. 154(b) by 0 days.

(21) Appl. No.: 11/091,970

(22) Filed: Mar. 28, 2005

(65) Prior Publication Data

US 2005/0228233 A1    Oct. 13, 2005

Related U.S. Application Data

(63) Continuation-in-part of application No. 10/745,068, filed on Dec. 22, 2003, which is a continuation of application No. 09/969,138, filed on Oct. 1, 2001, now Pat. No. 6,692,434.

(60) Provisional application No. 60/556,967, filed on Mar. 26, 2004, provisional application No. 60/236,584, filed on Sep. 29, 2000.

(51) Int. Cl.
*A61B 17/02* (2006.01)

(52) U.S. Cl. .................................... 600/210

(58) Field of Classification Search ............... 600/201, 600/210, 213, 214, 217, 219, 235
See application file for complete search history.

(56) References Cited

U.S. PATENT DOCUMENTS

| 569,839 A | 10/1896 | Roeloffs |
| 3,467,079 A * | 9/1969 | James ..................... 600/210 |
| 3,470,872 A | 10/1969 | Grieshaber |
| 3,875,595 A | 4/1975 | Froning |
| 4,041,939 A | 8/1977 | Hall |
| 4,232,660 A | 11/1980 | Coles |
| 4,440,168 A | 4/1984 | Warren |
| 4,481,947 A | 11/1984 | Chester |
| 4,545,374 A | 10/1985 | Jacobson |
| 4,573,448 A | 3/1986 | Kambin |

(Continued)

FOREIGN PATENT DOCUMENTS

EP        0820731        5/2003

(Continued)

OTHER PUBLICATIONS

U.S. Appl. No. 11/069,390, filed Mar. 1, 2005, Ritland.

(Continued)

*Primary Examiner*—Cary E. O'Connor
(74) *Attorney, Agent, or Firm*—Sheridan Ross P.C.

(57) ABSTRACT

A retractor is provided for performing spinal surgery with a minimal approach, and which spares the lumbar muscles from surgical disruption. A preferred embodiment includes a blade having first and second faces wherein the faces are positioned substantially transverse to one another, and wherein at least one of the faces has a tapered width. Alternatively, both the first and second faces are tapered. Additionally, a third face positioned transverse to the first face and substantially parallel to the third face may be incorporated into the retractor. The second face also preferably includes at least one tooth, and more preferably, a plurality of teeth at its distal end for laterally engaging an articular process of a vertebra of the spine.

13 Claims, 7 Drawing Sheets

U.S. PATENT DOCUMENTS

| | | |
|---|---|---|
| 4,617,922 A | 10/1986 | Griggs |
| 4,620,460 A | 11/1986 | Gonzales, Jr. |
| 4,686,972 A | 8/1987 | Kurland |
| 4,736,738 A | 4/1988 | Lipovsek |
| 4,743,260 A | 5/1988 | Burton |
| 4,747,394 A | 5/1988 | Watanabe |
| 4,798,111 A | 1/1989 | Cheeseman |
| 4,803,976 A | 2/1989 | Frigg |
| 4,817,587 A | 4/1989 | Janese |
| 4,862,891 A | 9/1989 | Smith |
| 4,863,423 A | 9/1989 | Wallace |
| 4,882,958 A | 11/1989 | McNeely |
| 5,002,542 A | 3/1991 | Frigg |
| 5,002,576 A | 3/1991 | Fuhrmann et al. |
| 5,026,373 A | 6/1991 | Ray et al. |
| 5,030,220 A | 7/1991 | Howland |
| 5,035,232 A | 7/1991 | Lutze et al. |
| 5,048,379 A | 9/1991 | Gramera |
| 5,052,373 A | 10/1991 | Michelson |
| 5,055,104 A | 10/1991 | Ray |
| 5,084,043 A | 1/1992 | Hertzmann |
| 5,098,435 A | 3/1992 | Stednitz |
| 5,106,376 A | 4/1992 | Mononen |
| 5,129,900 A | 7/1992 | Asher et al. |
| 5,133,720 A | 7/1992 | Greenberg |
| 5,135,525 A | 8/1992 | Biscoping |
| 5,148,724 A | 9/1992 | Rexford |
| 5,158,543 A | 10/1992 | Lazarus |
| 5,195,541 A | 3/1993 | Obenchain |
| 5,275,600 A | 1/1994 | Allard et al. |
| 5,275,611 A | 1/1994 | Behl |
| 5,279,567 A | 1/1994 | Ciaglia |
| 5,292,309 A | 3/1994 | Van Tassel |
| 5,303,694 A | 4/1994 | Mikhail |
| 5,306,309 A | 4/1994 | Wagner et al. |
| 5,312,360 A | 5/1994 | Behl |
| 5,312,405 A | 5/1994 | Korotko et al. |
| 5,356,413 A | 10/1994 | Martins et al. |
| 5,363,841 A | 11/1994 | Coker |
| 5,415,661 A | 5/1995 | Holmes |
| 5,431,639 A | 7/1995 | Shaw |
| 5,431,651 A | 7/1995 | Goble |
| D361,381 S | 8/1995 | Koros et al. |
| 5,439,464 A | 8/1995 | Shapiro |
| 5,466,238 A | 11/1995 | Lin |
| 5,472,426 A | 12/1995 | Bonati |
| 5,474,555 A | 12/1995 | Puno et al. |
| 5,484,440 A | 1/1996 | Allard |
| 5,489,274 A | 2/1996 | Chu |
| 5,489,308 A | 2/1996 | Kuslich et al. |
| 5,512,038 A | 4/1996 | O'Neal et al. |
| 5,558,622 A * | 9/1996 | Greenberg .................. 600/237 |
| 5,565,502 A | 10/1996 | Glimcher et al. |
| 5,591,166 A | 1/1997 | Bernhardt et al. |
| 5,591,235 A | 1/1997 | Kuslich |
| 5,593,409 A | 1/1997 | Michelson |
| 5,601,550 A | 2/1997 | Esser |
| 5,611,778 A | 3/1997 | Brinon |
| 5,628,740 A | 5/1997 | Mullane |
| 5,643,263 A | 7/1997 | Simonson |
| 5,643,264 A | 7/1997 | Sherman et al. |
| 5,645,599 A | 7/1997 | Samani |
| 5,683,463 A | 11/1997 | Godefroy et al. |
| 5,687,739 A | 11/1997 | McPherson |
| 5,690,632 A | 11/1997 | Schwartz et al. |
| 5,691,397 A | 11/1997 | Glimcher et al. |
| 5,702,455 A | 12/1997 | Saggar |
| 5,716,415 A | 2/1998 | Steffee |
| 5,725,528 A | 3/1998 | Errico et al. |
| 5,735,899 A | 4/1998 | Schwartz et al. |
| 5,743,853 A | 4/1998 | Lauderdale |
| 5,746,720 A | 5/1998 | Stouder, Jr. |
| 5,746,741 A | 5/1998 | Kraus et al. |
| 5,752,957 A | 5/1998 | Ralph et al. |
| 5,766,221 A | 6/1998 | Benderev et al. |
| 5,766,253 A | 6/1998 | Brosnahan, III |
| 5,782,832 A | 7/1998 | Larsen et al. |
| 5,785,710 A | 7/1998 | Michelson |
| 5,792,044 A | 8/1998 | Foley |
| 5,800,435 A | 9/1998 | Errico et al. |
| D399,955 S | 10/1998 | Koros et al. |
| 5,816,257 A | 10/1998 | Chin |
| 5,827,328 A | 10/1998 | Buttermann |
| 5,836,948 A | 11/1998 | Zucherman et al. |
| RE36,020 E | 12/1998 | Moore et al. |
| 5,851,207 A | 12/1998 | Cesarone |
| 5,860,977 A | 1/1999 | Zucherman et al. |
| 5,865,847 A | 2/1999 | Kohrs et al. |
| 5,865,848 A | 2/1999 | Baker |
| 5,876,404 A | 3/1999 | Zucherman et al. |
| 5,882,344 A | 3/1999 | Stouder, Jr. |
| 5,885,285 A | 3/1999 | Simonson |
| 5,885,299 A | 3/1999 | Winslow et al. |
| 5,885,300 A | 3/1999 | Tokuhashi et al. |
| 5,891,147 A | 4/1999 | Moskovitz et al. |
| 5,895,352 A | 4/1999 | Kleiner |
| 5,895,390 A | 4/1999 | Moran et al. |
| 5,897,593 A | 4/1999 | Kohrs et al. |
| 5,899,901 A | 5/1999 | Middleton |
| 5,902,231 A | 5/1999 | Foley |
| 5,906,616 A | 5/1999 | Pavlov et al. |
| 5,913,818 A | 6/1999 | Co et al. |
| 5,928,139 A | 7/1999 | Koros |
| 5,928,233 A | 7/1999 | Apfelbaum et al. |
| 5,944,658 A | 8/1999 | Koros et al. |
| 5,954,635 A | 9/1999 | Foley |
| 5,954,671 A | 9/1999 | O'Neil |
| 5,967,970 A | 10/1999 | Cowan |
| 5,968,098 A | 10/1999 | Winslow |
| 5,971,920 A | 10/1999 | Nagel |
| 5,976,146 A | 11/1999 | Ogawa |
| 5,984,924 A | 11/1999 | Asher et al. |
| 5,996,447 A | 12/1999 | Bayouth |
| 5,997,539 A | 12/1999 | Errico et al. |
| 6,007,487 A | 12/1999 | Foley et al. |
| 6,010,520 A | 1/2000 | Pattison |
| 6,045,579 A | 4/2000 | Hochshuler et al. |
| 6,048,342 A | 4/2000 | Zucherman et al. |
| 6,050,997 A | 4/2000 | Mullane |
| 6,063,088 A | 5/2000 | Winslow |
| 6,068,630 A | 5/2000 | Zucherman et al. |
| 6,074,390 A | 6/2000 | Zucherman et al. |
| 6,074,393 A | 6/2000 | Sitoto |
| 6,080,155 A | 6/2000 | Michelson |
| 6,080,193 A | 6/2000 | Hochshuler et al. |
| 6,081,741 A | 6/2000 | Hollis |
| 6,083,225 A | 7/2000 | Winslow et al. |
| 6,090,112 A | 7/2000 | Zucherman et al. |
| 6,102,948 A | 8/2000 | Brosnahan, III |
| 6,113,602 A | 9/2000 | Sand |
| 6,117,137 A | 9/2000 | Halm et al. |
| 6,117,174 A | 9/2000 | Nolan |
| 6,120,434 A | 9/2000 | Kimura |
| 6,120,506 A | 9/2000 | Kohrs et al. |
| 6,123,705 A | 9/2000 | Michelson |
| 6,123,706 A | 9/2000 | Lange |
| 6,132,430 A | 10/2000 | Wagner |
| D433,296 S | 11/2000 | Yamakawa |
| 6,149,652 A | 11/2000 | Zucherman et al. |
| 6,149,686 A | 11/2000 | Kuslich et al. |
| 6,152,871 A | 11/2000 | Foley |
| 6,152,926 A | 11/2000 | Zucerman et al. |
| 6,156,006 A | 12/2000 | Brosens |
| 6,156,038 A | 12/2000 | Zucherman et al. |

| | | |
|---|---|---|
| 6,159,179 A | 12/2000 | Simonson |
| 6,162,170 A | 12/2000 | Foley |
| 6,162,236 A | 12/2000 | Osada |
| D436,513 S | 1/2001 | Yamakawa |
| 6,176,823 B1 | 1/2001 | Foley |
| 6,179,838 B1 | 1/2001 | Fiz |
| D438,074 S | 2/2001 | Marr |
| 6,183,471 B1 | 2/2001 | Zucherman et al. |
| 6,190,387 B1 | 2/2001 | Zucherman et al. |
| 6,197,002 B1 | 3/2001 | Peterson |
| 6,206,822 B1 | 3/2001 | Foley |
| 6,206,826 B1 | 3/2001 | Mathews et al. |
| 6,206,885 B1 | 3/2001 | Ghahremani et al. |
| 6,206,922 B1 | 3/2001 | Zdeblick et al. |
| 6,206,923 B1 | 3/2001 | Boyd et al. |
| 6,210,413 B1 | 4/2001 | Justis et al. |
| 6,214,004 B1 | 4/2001 | Coker |
| 6,217,509 B1 | 4/2001 | Foley |
| 6,224,597 B1 | 5/2001 | Coker |
| 6,224,608 B1 | 5/2001 | Ciccolella |
| 6,224,631 B1 | 5/2001 | Kohrs |
| 6,235,030 B1 | 5/2001 | Zucherman et al. |
| 6,238,397 B1 | 5/2001 | Zucherman et al. |
| 6,245,072 B1 | 6/2001 | Zdeblick et al. |
| 6,248,106 B1 | 6/2001 | Ferree |
| 6,258,097 B1 | 7/2001 | Cook |
| 6,261,287 B1 | 7/2001 | Metz-Stavenhagen |
| 6,264,658 B1 | 7/2001 | Lee et al. |
| 6,267,763 B1 | 7/2001 | Castro |
| 6,267,764 B1 | 7/2001 | Elberg |
| 6,267,765 B1 | 7/2001 | Taylor et al. |
| 6,270,498 B1 | 8/2001 | Michelson |
| 6,283,966 B1 | 9/2001 | Houfburg |
| 6,287,313 B1 | 9/2001 | Sasso |
| 6,287,343 B1 | 9/2001 | Kuslich et al. |
| 6,290,700 B1 | 9/2001 | Schmotzer |
| 6,293,949 B1 | 9/2001 | Justis et al. |
| 6,296,609 B1 | 10/2001 | Brau |
| 6,312,432 B1 | 11/2001 | Leppelmeier |
| 6,332,883 B1 | 12/2001 | Zucherman et al. |
| 6,342,057 B1 | 1/2002 | Brace |
| 6,348,058 B1 | 2/2002 | Melkent et al. |
| 6,354,176 B1 | 3/2002 | Nordlin |
| 6,368,350 B1 | 4/2002 | Erickson et al. |
| 6,368,351 B1 | 4/2002 | Glenn et al. |
| 6,371,959 B1 | 4/2002 | Trice |
| 6,371,968 B1 | 4/2002 | Kogasaka |
| 6,391,058 B1 | 5/2002 | Kuslich et al. |
| 6,395,033 B1 | 5/2002 | Pepper |
| 6,418,821 B1 | 7/2002 | Yamakawa |
| 6,428,472 B1 | 8/2002 | Haas |
| 6,440,169 B1 | 8/2002 | Elberg et al. |
| 6,443,989 B1 | 9/2002 | Jackson |
| 6,461,330 B1 | 10/2002 | Miyagi |
| D466,766 S | 12/2002 | Marty |
| 6,520,907 B1 | 2/2003 | Foley |
| 6,524,238 B1 | 2/2003 | Velikaris et al. |
| 6,530,926 B1 | 3/2003 | Davison |
| 6,540,756 B1 | 4/2003 | Vaughan |
| 6,551,320 B1 | 4/2003 | Lieberman |
| 6,565,569 B1 | 5/2003 | Assaker et al. |
| 6,692,434 B1 | 2/2004 | Ritland |
| 6,736,816 B1 | 5/2004 | Ritland |
| 2001/0005796 A1 | 6/2001 | Zdeblick et al. |
| 2001/0010021 A1 | 7/2001 | Boyd et al. |
| 2001/0012942 A1 | 8/2001 | Estes |
| 2001/0027320 A1 | 10/2001 | Sasso |
| 2001/0047207 A1 | 11/2001 | Michelson |
| 2002/0011135 A1 | 1/2002 | Hall |
| 2002/0016592 A1 | 2/2002 | Branch |
| 2002/0022764 A1 | 2/2002 | Smith |
| 2002/0029082 A1 | 3/2002 | Muhanna |
| 2002/0049368 A1 | 4/2002 | Ritland |
| 2002/0058948 A1 | 5/2002 | Arlettaz |
| 2002/0068973 A1 | 6/2002 | Jackson |
| 2002/0068975 A1 | 6/2002 | Teitelbaum et al. |
| 2002/0077632 A1 | 6/2002 | Tsou |
| 2002/0082695 A1 | 6/2002 | Neumann |
| 2002/0107571 A1 | 8/2002 | Foley |
| 2002/0107572 A1 | 8/2002 | Foley et al. |
| 2002/0120270 A1 | 8/2002 | Trieu et al. |
| 2002/0123668 A1 | 9/2002 | Ritland |
| 2002/0143235 A1 | 10/2002 | Pagliuca |
| 2003/0083688 A1 | 5/2003 | Simonson |
| 2003/0083689 A1 | 5/2003 | Simonson |
| 2003/0093078 A1 | 5/2003 | Ritland |
| 2003/0144665 A1 | 7/2003 | Munting |
| 2003/0171749 A1 | 9/2003 | Le Couedic et al. |
| 2003/0171751 A1 | 9/2003 | Ritland |
| 2003/0187431 A1 | 10/2003 | Simonson |
| 2003/0191470 A1 | 10/2003 | Ritland |
| 2003/0220689 A1 | 11/2003 | Ritland |
| 2003/0236447 A1 | 12/2003 | Ritland |
| 2004/0002708 A1 | 1/2004 | Ritland |
| 2004/0106997 A1 | 6/2004 | Lieberson |
| 2004/0172023 A1 | 9/2004 | Ritland |
| 2004/0181223 A1 | 9/2004 | Ritland |
| 2004/0254428 A1 | 12/2004 | Ritland |
| 2005/0004593 A1 | 1/2005 | Simonson |
| 2005/0020920 A1 | 1/2005 | Ritland |

FOREIGN PATENT DOCUMENTS

| | | |
|---|---|---|
| WO | WO 00/18306 | 4/2000 |
| WO | WO 02/02022 | 1/2002 |
| WO | WO 02/07621 | 1/2002 |
| WO | WO 02/060330 | 8/2002 |
| WO | WO 03/026523 | 4/2003 |
| WO | WO 03/073908 | 9/2003 |
| WO | WO 03/094699 | 11/2003 |
| WO | WO 04/075778 | 9/2004 |
| WO | WO 04/089244 | 10/2004 |

OTHER PUBLICATIONS

U.S. Appl. No. 10/745,068, filed Feb. 10, 2004, Ritland.
Caspar; "Technique of Microsurgery: Microsurgery of the Lumbar Spine: Principles and Techniques in Spine Surgery"; *Aspen Publications*; 1990; 105-122.
Hilton et al.; "Meditronic Sofamor Danek METRX Microdiscectomy Surgical Technique Brochure"; 2000.
Kambin; "Arthroscopic Microdiscectomy: Minimal Intervention in Spinal Surgery"; *National Library of Medicine*; 1991; 67-100.
Kambin; "Percutaneous Posterolateral Discectomy"; *Clinical Orthopaedics and Related Research, Section II*; 145-154119.
Savitz; "Same-Day Microsurgical Arthroscopic Latera-Approach Laser-Assisted (SMALL) Fluroscopic Discectomy"; *Journal of Neurosurgery*; Jun. 1994; 1039-1045.
Schaffer et al.; "Percutaneous Posterolateral Lumbar Discectomy and Decompression with a 6.9 Millimeter Cannula"; *Journal of Bone and Joint Surgery*; 1991; 822-831.
Sofamor Danek Video Systems Brochure.
Wiltse; "New Uses and Refinements of the Paraspinal Approach to the Lumbar Spine"; *Spine*; 1988; 13(6):696-706.

* cited by examiner

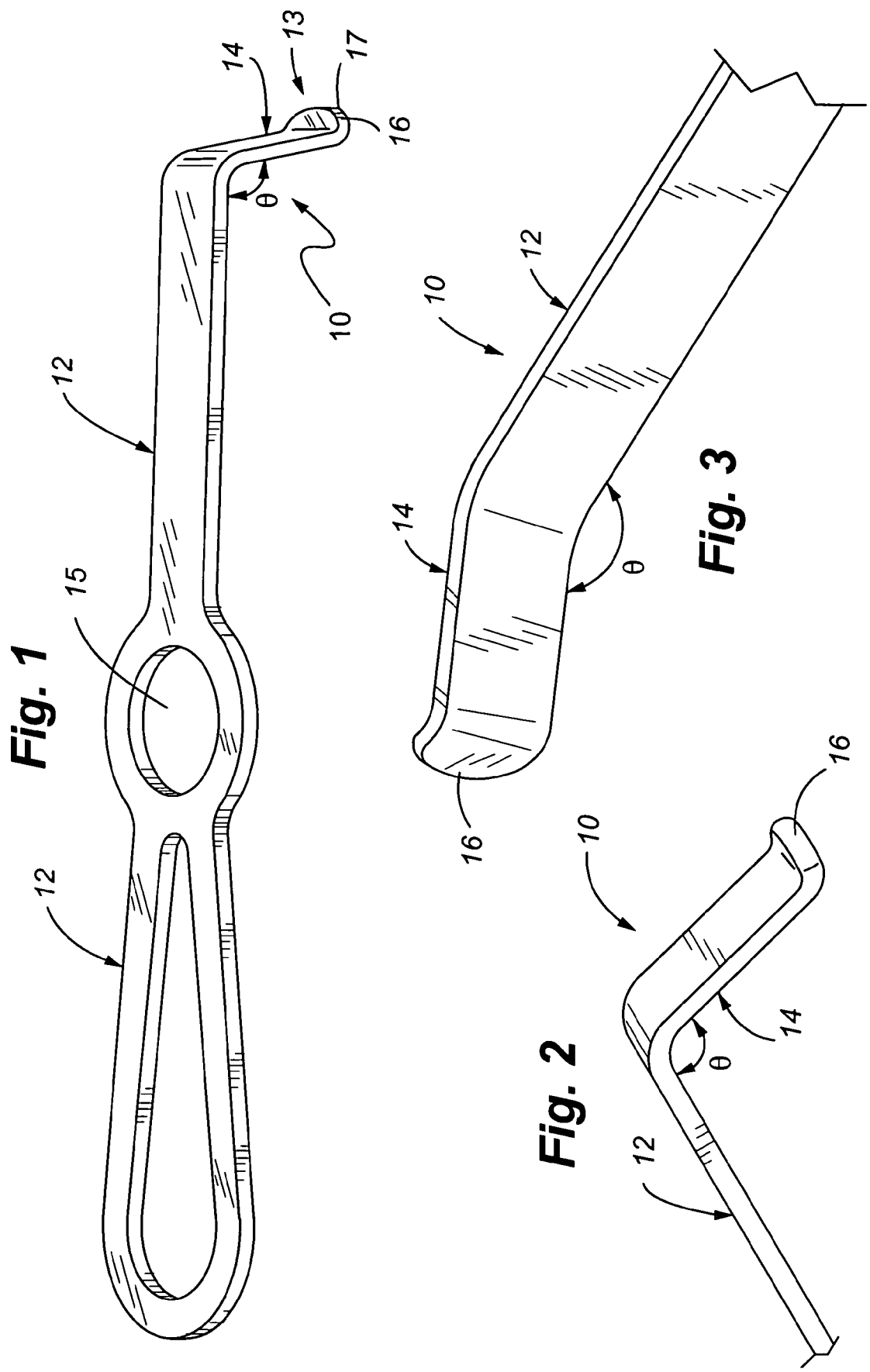

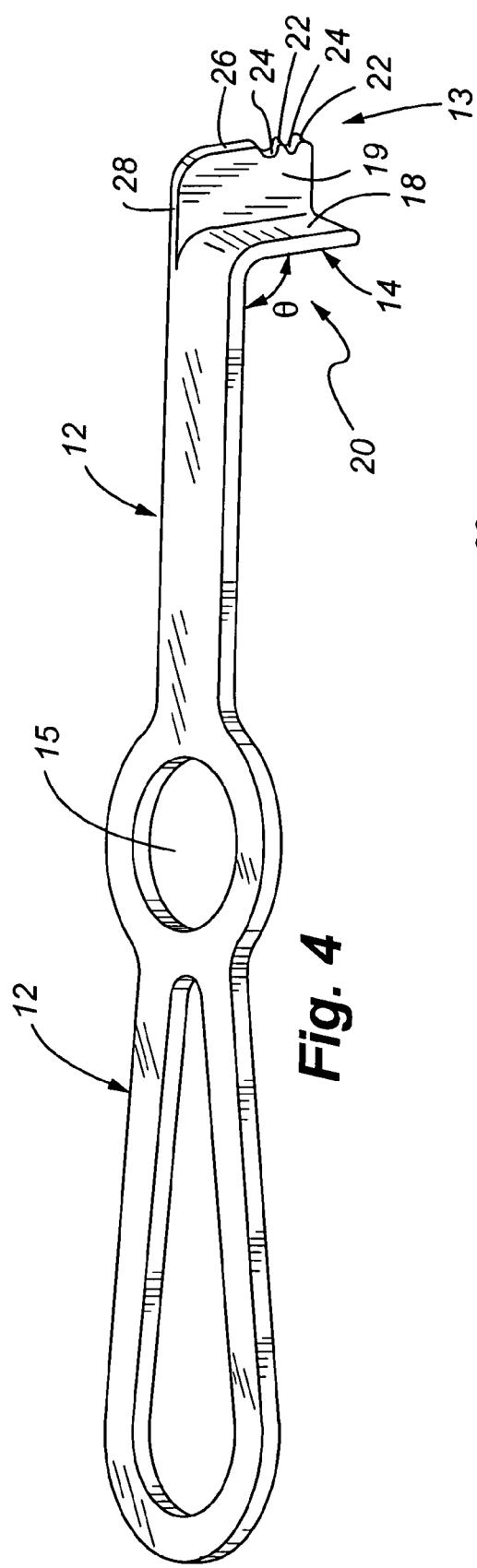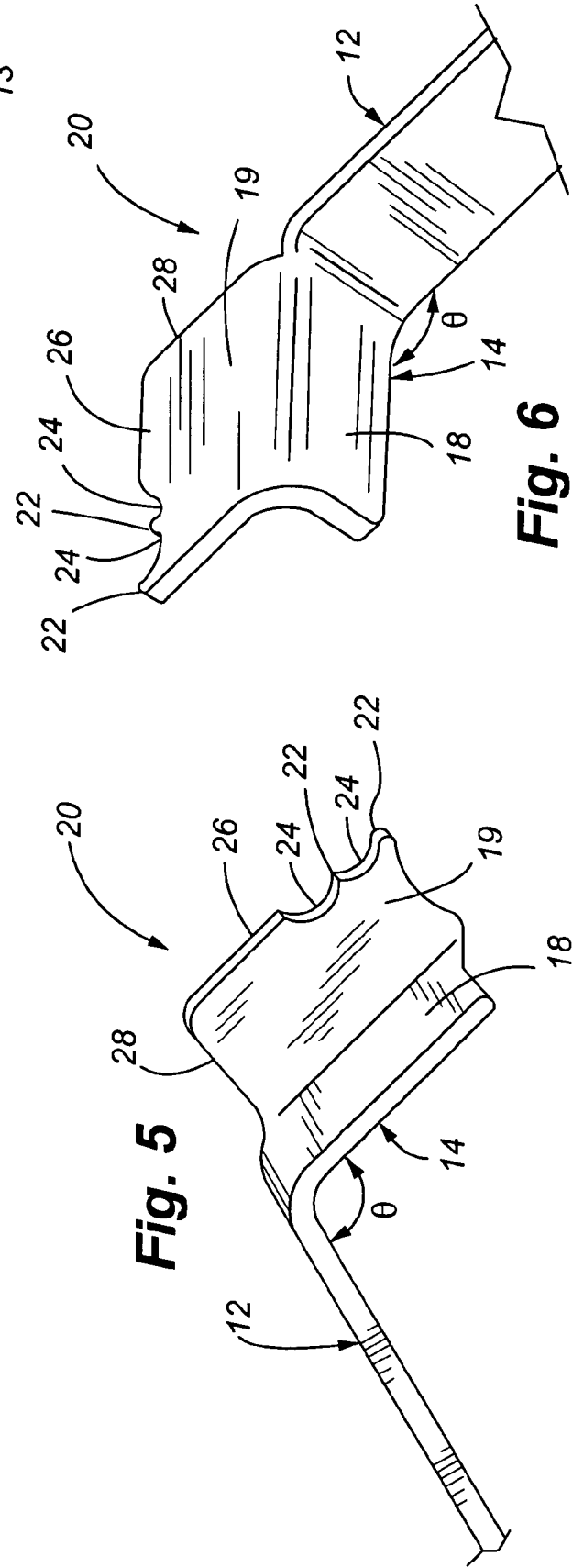

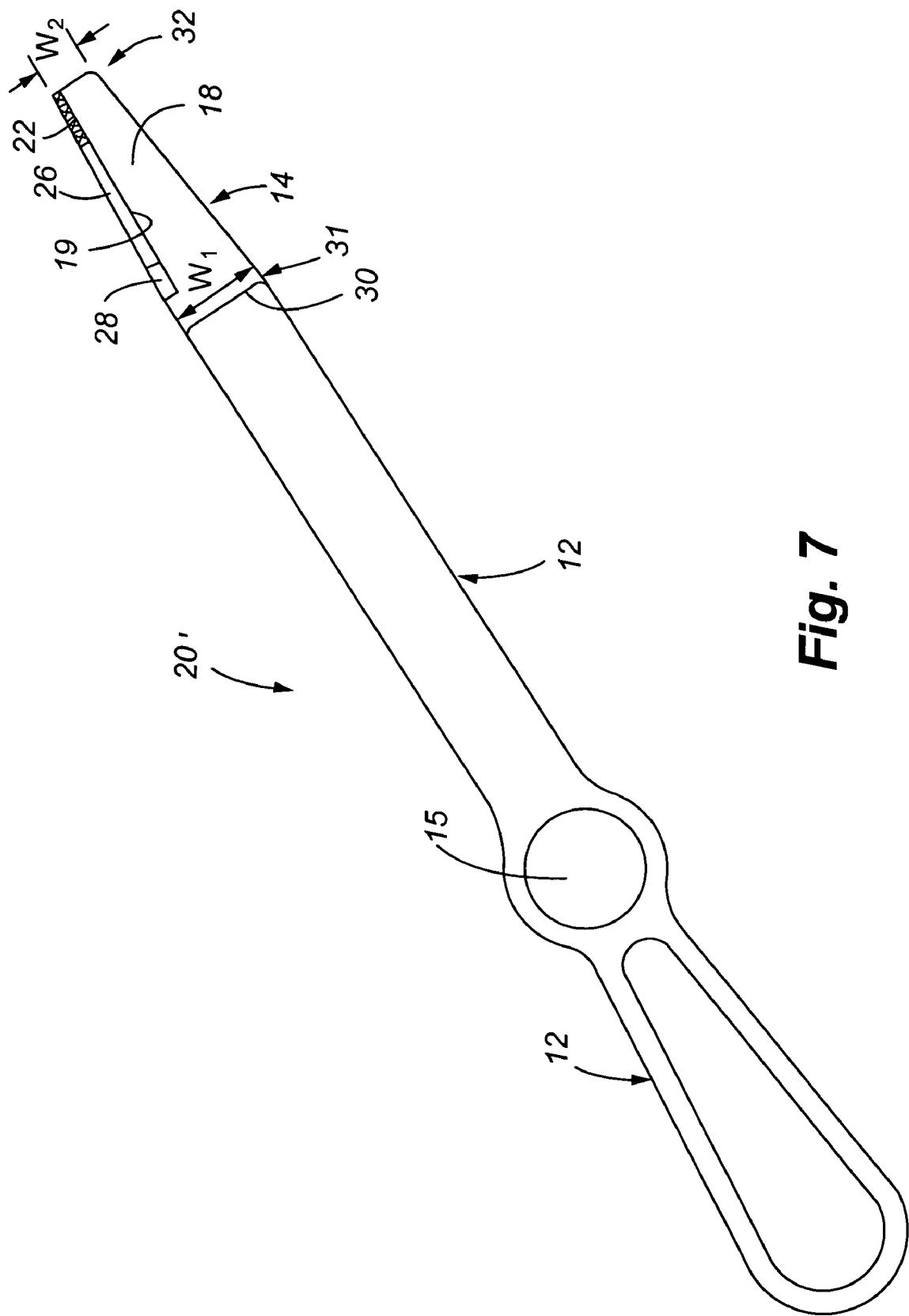

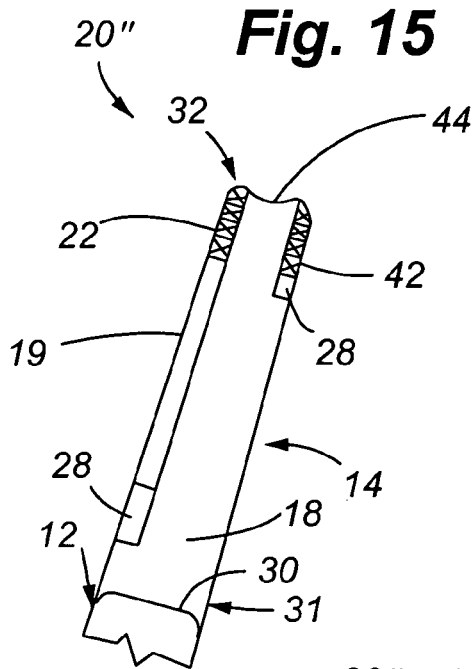
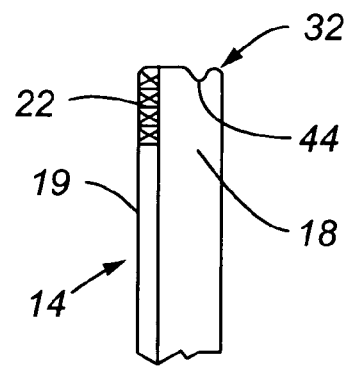
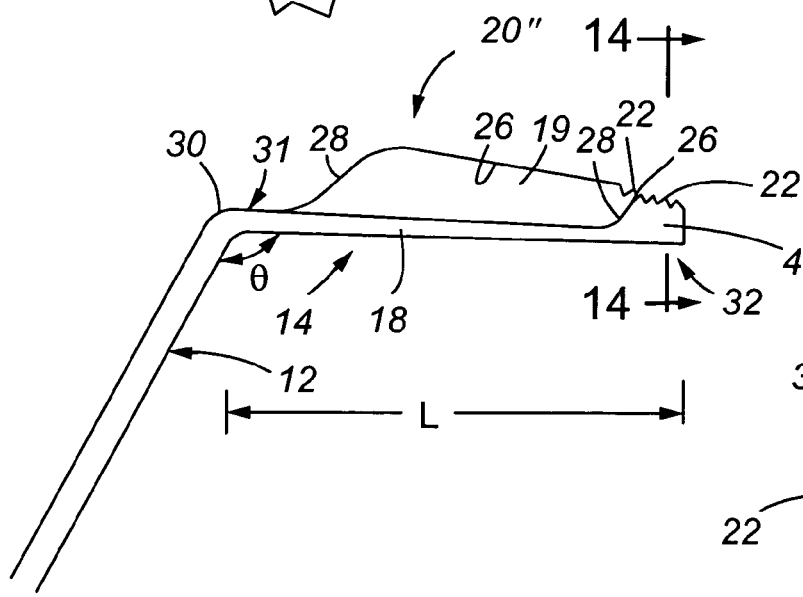
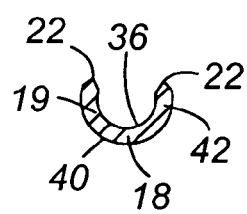
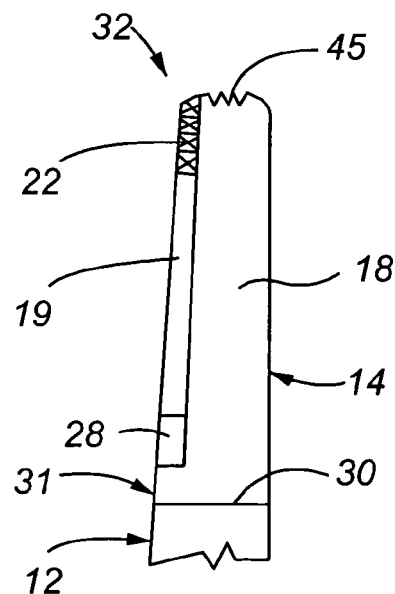

METHOD AND DEVICE FOR MICROSURGICAL INTERMUSCULAR SPINAL SURGERY

CROSS REFERENCE TO RELATED APPLICATIONS

This application is a continuation-in-part of prior U.S. patent application Ser. No. 10/745,068 filed Dec. 22, 2003, pending which is a continuation of U.S. patent application Ser. No. 09/969,138 filed on Oct. 1, 2001 (now U.S. Pat. No. 6,692,434 which issued Feb. 17, 2004), which claimed the benefit of U.S. Provisional Patent Application No. 60/236,584 filed on Sep. 29, 2000; in addition, the present application claims the benefit of U.S. Provisional Application No. 60/556,967 filed Mar. 26, 2004. The entire disclosures of these applications are considered to be part of the disclosure of the present application and are hereby incorporated by reference in their entirety.

FIELD OF THE INVENTION

The present invention is directed to a method and device for microsurgical intermuscular spinal surgery.

BACKGROUND OF THE INVENTION

In performing surgery on the spine, including the lumbar vertebrae, retractors are used to maintain necessary exposure and to keep the muscles out of the surgical field. In general, it is desirable to use a retractor to engage the lateral aspect of the facet as a point for leverage for retraction of the paraspinal muscles. Results of posterior lumbar fusion have frequently been compromised by residuals from muscular and neurovascular disruption accompanying arthrodesis. An approach along the lateral aspect of the multifidus avoids disruption of the dorsal lumbar musculature and allows for segmental pedicle fixation without disturbing the neurovascular supply to the erector spinae or multifidus. Detachment of the segmental insertion of the multifidus to the mamillary process provides access for a microsurgical transforaminal interbody fusion.

Present techniques of lumbar arthrodesis including instrumentation and interbody fusion provide a reasonable expectation of fusion with surgery; however, outcomes remain limited by pain and adjacent segment failure. To the extent this results from fusion it may be unavoidable. Limitations from denervation, devascularization and disconnection of lumbar musculature and the disruption of musculoskeletal integrity of adjacent segments may be largely avoidable.

For pedicle fixation, a screw having a diameter of 4 to 8 mm is generally used. For heretofore available retractors, more retraction than necessary was performed and the ability to specifically retract requisite structures was impaired. Specifically, the small muscles traversing the transverse process were more difficult to engage and may have been damaged by excess retraction. Additionally, a larger retractor was more difficult to place in the intermuscular plane opened for access.

There is, therefore, a long-felt but unsolved need for a method and device in order to perform an instrumented lumbar arthrodesis with a minimal approach which spares the lumbar muscles from surgical disruption.

SUMMARY OF THE INVENTION

One method of retraction is to use a muscle splitting or intermuscular approach to access the spine for fixation and for interbody fusion or dynamic fixation. An angled retractor offers the advantage of being able to be manipulated by a surgeon to engage the implant construct and retract the muscles medially to provide a window of access medial to the implant construct with secure fixation against the implant. This device enables a surgeon to access the pedicle for screw placement.

Preferred embodiments of the present invention allow a surgeon to minimize the exposure needed for surgery, thereby minimizing the necessary retraction, and also allows the device to be used with a guide wire or drill with a minimum approach. The retractors of the present invention can be made in a right and left configuration, and the blade is typically used in lengths ranging from about 25 to 90 mm from its proximal end to its distal end. In addition, the blade is preferably angled relative to the attached handle at an angle of about 90 degrees or greater, and more preferably, at an angle of about 115 degrees to correspond to the typically needed trajectory for screw placement into the lumbar spine. In addition, a separate aspect of the present invention is a blade having a width of about 12 to 16 mm to provide an appropriate window for a typical polyaxial screw and with one or a plurality of points to engage and stabilize the retractor.

Thus, in one embodiment of the present invention, a tissue retractor for use in surgery of a spine is provided, wherein the retractor includes a handle and a blade connected to the handle at an intersection. Preferably, the handle forms an angle with the blade of between about 90 and 135 degrees, and more preferably, the handle forms an angle with the blade of about 115 degrees. The blade includes a first face and a second face positioned transverse to the first face, and more preferably, the first face is substantially perpendicular to the second face with a quarter-rounded bend interconnecting the first face to the second face. In accordance with embodiments of the present invention, the second face has an upper proximal edge spaced apart from the intersection, and the second face also preferably has a variable width, with a first larger width at a location positioned proximally of a second narrower width at the distal end of the second face. In accordance with embodiments of the present invention, the distal end of the second face includes at least one co-planar forward projecting tooth for laterally engaging an articular complex of a vertebra of the spine. In addition, the first and second faces of the blade preferably include a partially rounded tip at the distal end of the blade. The first face optionally includes a terminal indentation or a distal tooth at the distal end of the blade, wherein the terminal indentation or distal tooth are adapted to engage a transverse process of the vertebra. The retractor optionally further includes a third face located transverse to the first face and opposite the second face, wherein the first face is substantially perpendicular to the third face with a quarter-rounded bend interconnecting the first face to the third face. In accordance with embodiments of the present invention, the first, second and third faces preferably form a U-shape, with the third face substantially parallel to the second face. Similar to the second face, the third face preferably includes at least one co-planar forward projecting tooth, and more preferably, a plurality of co-planar forward projecting teeth. In one example of this embodiment, the third face further includes an upper proximal edge located distally of the upper proximal edge of the second face. The first face of the blade may also have a variable width, preferably including a first larger width at a location positioned proximally of a second narrower width at a distal end of the first face. The retractor preferably includes a partially rounded smooth outer blade surface that allows tissue to easily slide along the outer surface of the retractor as the retractor is inserted or withdrawn from a surgical site. Finally, the retractor may optionally include a tool groove along its first face.

In accordance with embodiments of the present invention, a retractor is provide wherein the retractor includes a handle and a blade connected to the handle, the blade including a first face and a second face positioned substantially perpendicular to the first face. In accordance with embodiments of the present invention, the second face includes at least one tooth for laterally engaging an articular process of a vertebra of the spine. The first face has a tapered width with a first larger width at a location positioned proximally of a second narrower width at a distal end of the first face, and the second face also has a tapered width with a larger width positioned proximally of a narrower width at a distal end of the second face. The retractor can be made in a left or a right hand configuration to accommodate approaching the spine from either side. When used in lumbar surgery, the blade preferably has a length between about 25 to 90 and the handle forms an angle with the blade of between about 90 and 135 degrees, and more preferably, the handle forms an angle with the blade of about 115 degrees. The blade preferably includes a curved transition between the first face and the second face. The curved transition can comprise a constant radius curve, or it can comprise a tapered conic section consistent with the taper of the first face and the taper of the second face. The retractor optionally includes a third face located transverse to the first face, wherein the first face is substantially perpendicular to the third face, and wherein the first, second, and third faces form a U-shaped interior surface. Similar to the second face, the third face preferably includes at least one co-planar forward projecting tooth, and more preferably, a plurality of co-planar forward projecting teeth. The retractor also preferably includes a partially rounded smooth outer blade surface that allows tissue to easily slide along the outer surface of the retractor as the retractor is inserted into or removed from a surgical site. Finally, the retractor may optionally include a tool groove along its first face.

Yet a further modified version of a retractor is provided, wherein the retractor includes a handle and a blade connected to the handle. In accordance with embodiments of the present invention, the blade includes a first planar surface for orienting substantially parallel to an axis of the spine, a second planar surface for orienting substantially perpendicular to the axis of the spine, and a third planar surface located substantially opposite at least a portion of the second planar surface and for orienting substantially perpendicular to the axis of the spine. A cylindrical or curved transition is located between the second, the first, and the third planar surfaces wherein a U-shaped blade portion is formed. In accordance with embodiments of the present invention, the second and third planar surfaces include a plurality of teeth pointing medially to engage an articular complex of the spine. In addition, at least the first and second planar surfaces have tapered widths wherein a proximal end of the first and second planar surfaces is wider than a distal end of the first and second planar surfaces. The tapered first and second planar surfaces provide a working window for a transverse process lateral to the articular complex. The first planar surface optionally includes a terminal indentation or a distal tooth at the tip of the distal end of the first planar surface, wherein the terminal indentation or distal tooth are adapted to engage the transverse process. In addition, the first planar surface may also optionally include a tool groove.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 1 is a side perspective view of one embodiment of a retractor of the present invention;

FIG. 2 is a partial perspective view of the blade of the retractor shown in FIG. 1;

FIG. 3 is a view of the blade as depicted in FIG. 2, but viewed from a reverse angle;

FIG. 4 is a side perspective view of a second embodiment of a retractor of the present invention;

FIG. 5 is a partial perspective view of the blade of the retractor shown in FIG. 4;

FIG. 6 is a view of the blade as depicted in FIG. 5, but viewed from a reverse angle;

FIG. 7 is a plan view of a modified version of the second embodiment shown in FIG. 4;

FIG. 13 is a partial side elevation view of yet a different modified version of the second embodiment shown in FIG. 4 with a third face incorporated into the blade;

FIG. 14 is a cross-section view of the blade of the retractor of FIG. 13 taken along line 14—14 of FIG. 13;

FIG. 15 is a partial plan view of a portion of the blade of the retractor shown in FIG. 13 with a relatively broad terminal indentation;

FIG. 16 is a partial plan view of a portion of the blade of the second embodiment with a relatively narrow terminal indentation;

FIG. 17 is a partial plan view of a blade of the second embodiment with a plurality of distal teeth shown at the distal end of the blade;

DETAILED DESCRIPTION OF THE INVENTION

Figures 8, 9, 10, 11, 12:
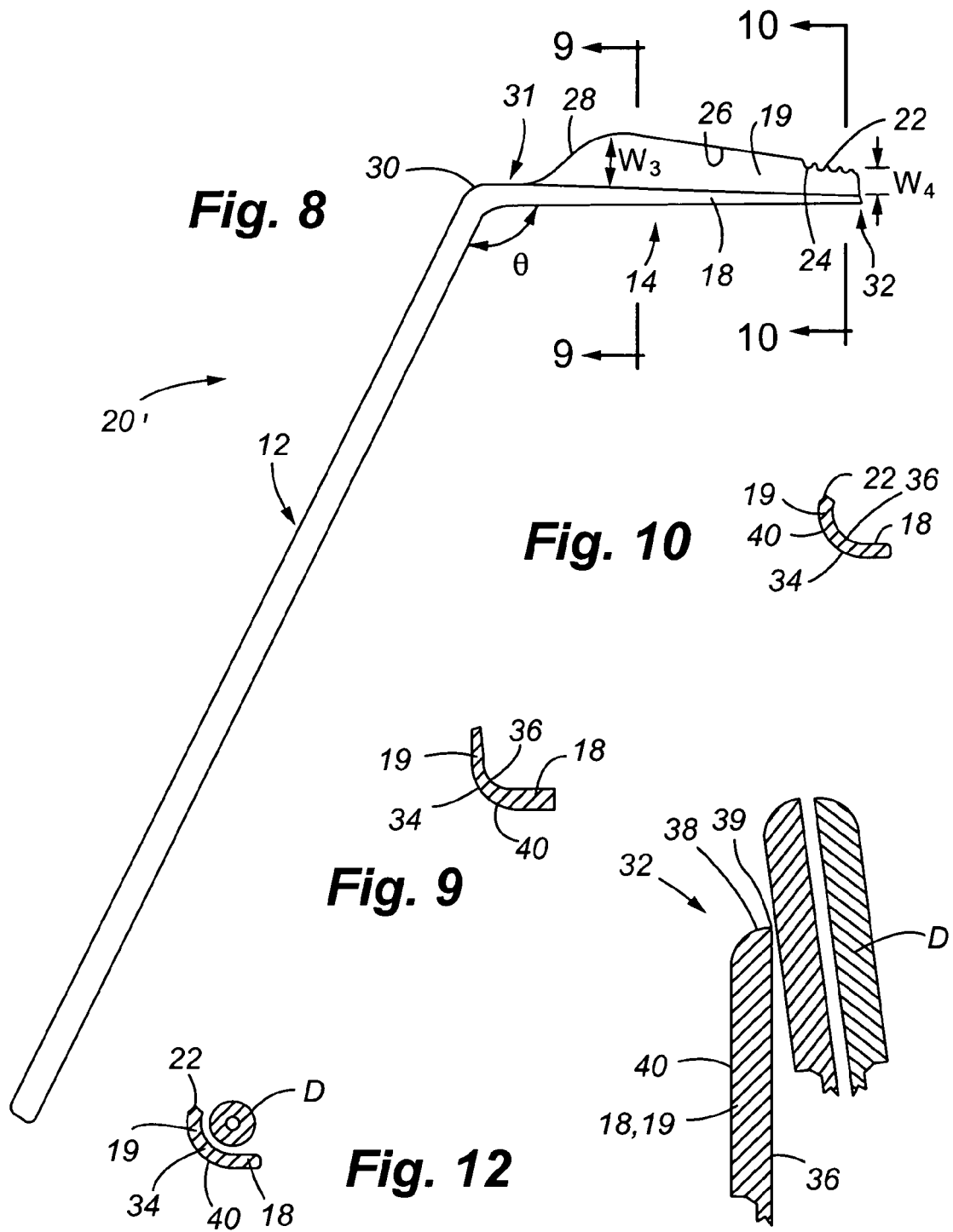
FIG. 8 is a side elevation view of the device shown in FIG. 7.
FIG. 9 is a cross-sectional view of the blade of the retractor of FIG. 8 taken along line 9—9 of FIG. 8.
FIG. 10 is a cross-sectional view of the blade of the retractor of FIG. 8 taken along line 10—10 of FIG. 8.
FIG. 11 is an enlarged side cross-sectional view of the tip of the distal end of either the first face or second face of the blade of the retractor of FIG. 8 with a cylindrical dilator.
FIG. 12 is a transverse cross-section view of the blade tip shown in FIG. 11 with a cylindrical dilator.

The present invention is directed to a device and a method for performing an instrumented lumbar interbody fusion or dynamic fixation utilizing a minimally invasive approach. The device used by the surgeon to perform the minimally invasive approach is a retractor, wherein the retractor has a number of structural features as set out below that enable the surgeon to use the retractor to perform a minimally invasive surgical procedure.

Referring now to FIGS. 1–3, a first embodiment of the present invention is illustrated and is generally directed to the use of a tissue retractor 10 for use in lumbar arthrodesis or dynamic fixation. For the first embodiment, retractor 10 includes a handle 12 at one end, and a retractor blade 14 at a second end. The handle 12 allows a surgeon to hold and manipulate the retractor 10 and thereby manipulate a functional tip 13 of the retractor 10 to work in the intermuscular plane, engage the articular complex, and provide working access for placement of an appropriate spinal construct. The handle 12 is approximately 23 cm in length, although this length can vary depending upon a surgeon's preferences for the handle size. The handle 12 is of conventional configuration for a surgical retractor handle, and it preferably includes a central aperture 15, that allows for attachment of a mechanical arm to secure the retractor in position, if desired. The handle may also incorporate components of an image guidance system (not shown), such as reflective spheres to thereby assist in guiding a tap or wire guide along the blade 14.

The retractor blade 14 is angled at approximately a 90 to 135 degree angle with respect to the handle 12. More specifically, the handle 12 and blade 14 are separated by an angle θ, where angle θ preferably is equal to or greater than about 90 degrees and less than or equal to about 135 degrees. More preferably, θ is about 115 degrees. Said differently, the blade 14 preferably projects forward approximately 25 degrees from a perpendicular to the handle 12, or approximately 115 degrees from the handle 12 itself. It is set to provide an appropriate angulation for pedicle access if the retractor 10 is engaged on the lateral aspect of the articular process and the handle 12 is pulled lateral to a horizontal position.

The retractor blade 14 has a depth so as to provide adequate retraction when performing a screw placement operation. More particularly, the length of the blade is preferably between about 25 to 90 mm in length, and more preferably, about 75 mm in length. The blade 14 of retractor 10 includes a hooked forward projecting prominence 16 to engage a lateral facet or muscle. The forward projecting prominence 16 has a width approximately equal to a width of the retractor blade 14, and has a semi-circular shaped front edge 17. The skin and lateral muscles act to maintain the tip engaged medially against the articular process.

Referring now to FIGS. 4–6, in a second preferred embodiment, retractor 20 has a similar handle 12 and has a blade 14 positioned at angle θ relative to handle 12, where angle θ preferably is again equal to or greater than about 90 degrees and less than or equal to about 135 degrees. More preferably, θ is about 115 degrees. The retractor blade 14 includes first and second faces 18 and 19, respectively, with the first face 18 preferably substantially perpendicular or transverse to the second face 19. The second face 19 preferably has at least one co-planar toothed structure 22, and more preferably, a plurality of toothed structures or teeth 22, such as two toothed structures shown in FIGS. 4–6, or alternatively, four toothed structures as shown in FIG. 8. The forward projecting teeth 22 serve to engage the lateral aspect of the articular complex when the retractor 20 is in use. The toothed structures 22 are preferably situated adjacent at least one co-planar indentation 24, and more preferably, a plurality of co-planar indentations 24. As shown in FIG. 5, in at least one preferred embodiment, the indentations 24 are semi-circular in shape. The toothed structures 22 and the indentations 24 are located along a lower portion of a forward projecting lateral edge 26 of the second face 19. Preferably, the forward projecting teeth 22 and the indentations 24 are present in about the distal 8 mm of the second face 19.

Referring now to FIGS. 7 and 8, a modification of the second embodiment of the invention is shown. In accordance with embodiments of the present invention, retractor 20' includes a blade 14 having a depth so as to provide adequate retraction when performing a screw placement operation. More particularly, the length L of the blade 14 is preferably between about 25 to 90 mm in length, and more preferably, about 75 mm in length.

In accordance with embodiments of the present invention, blade 14 of retractor 20' includes a first face 18 and a second face 19 that preferably has a variable width along its length. As shown in FIG. 8, the second face 19 of the retractor 20' has a sloped forward projecting lateral edge 26 relative to a plane occupied by first face 18. Preferably, the second face 19 increases in width, at least along a portion of its length, from its distal end 32 toward the intersection 30. This feature allows the retractor 20' to have sufficient size at the interior surgical work site for visualization and tool insertion by the surgeon, but also provides an increase in the dimension of the proximal end 31 of the second face 19 such that additional light, an increased access space, and an increased working angle is provided at the proximal end 31 of the blade 14.

In addition, in one preferred embodiment shown in FIG. 7 and 8, second face 19 does not extend proximally to the handle 12. More particularly, second face 19 includes an upper or proximal edge 28 preferably spaced apart from an intersection 30 between the handle 12 and blade 14. Thus, referring to retractor 20 shown in FIGS. 4–6, second face 19 can have a proximal edge 28 that extends to the intersection 30 between handle 12 and blade 14. Alternately, as shown in FIGS. 7 and 8, retractor 20' can have a proximal edge 28 that is spaced apart from the intersection 30 between handle 12 and blade 14. Retractors 20 and 20' may be provided in a left or a right hand configuration, and therefore, can be used to approach either side of the spine.

Still referring to FIG. 7, although not required, in accordance with embodiments of the present invention, the first face 18 of retractor 20' preferably has a variable width, and more preferably yet, a tapered shape. More particularly, first face 18 preferably has a first width $W_1$ near the intersection 30 between handle 12 and blade 14 that is wider than a second width $W_2$ located at its distal end 32. The changing width of first face 18 is preferably at a constant rate between its proximal end 31 and its distal end 32. For one preferred example of this embodiment used in lumbar surgery, first face 18 of retractor 20' has a first width $W_1$ of about 16 mm near intersection 30, narrowing at a substantially constant rate to a second width $W_2$ of about 7 mm at its distal end 32.

Referring again to FIG. 8, and in accordance with embodiments of the present invention, although second face 19 may have a substantially constant width, as shown in the embodiment depicted in FIGS. 4–6, for retractor 20', the second face 19 may have a variable width, or alternatively, a tapered width along its length as shown in FIG. 8. More particularly, second face 19 preferably has a first width $W_3$ near its proximal edge 28 that is wider than a second width $W_4$ located at its distal end 32. The changing width of second face 19 is preferably at a substantially constant rate between its first width $W_3$ and its distal end 32. The proximal edge 28 of second face 19 preferably increases from a width of zero at some point spaced apart from intersection 30, to its greatest width $W_3$ where the proximal edge 28 meets with the sloped forward projecting lateral edge 26 of second face 19. For one preferred example of this embodiment used in lumbar surgery, second face 19 of retractor 20' has a first width $W_3$ of about 16 mm, narrowing at a constant rate to its second width $W_4$ of about 7 mm at its distal end 32.

Referring still to FIG. 8, as noted above, the second face 19 of bade 14 is preferably situated substantially perpendicular or transverse to first face 18. In addition, as shown in FIG. 9, the transition from first face 18 to second face 19 preferably includes about a 90 degree curvature transition or a quarter-rounded bend 34. The quarter-rounded bend 34 preferably extends from where the proximal edge 28 of second face 19 joins with first face 18 to the distal end 32 of first face 18 and second face 19, as shown in FIG. 10. The curvature or quarter-rounded bend 34 between the first face 18 and the second face 19 can take the form of a constant radius curve, or when both the first face 18 and the second face 19 are tapered, the curved transition can take the form of a tapered conic section consistent with the taper of the first face 18 and the taper of the second face 19.

In accordance with embodiments of the present invention, the curvature transition or quarter-rounded bend 34 preferably includes an interior surface 36 that smoothly transitions in a curved manner between first face 18 and second face 19. The curved interior surface 36 is, therefore, shaped to receive a cylindrical dilator D. Cylindrical dilators D are commonly used to provide access to an interior surgical site. For example, a guide wire or drill bit may initially be placed, and then subsequently, one or a series of cylindrical dilators can be placed over the guide wire to provide increasing spacial access. Thus, where a guide wire has been placed and subsequent access for tapping and/or screw placement is needed, a dilator D or series of cylindrical dilators may be slipped over the wire. The retractor may then be placed against the dilator D and slid into position.

As shown in FIG. 11, the retractor 20' features a distal end 32 that preferably includes a partially round tip 38 on both first face 18 and second face 19. When a dilator is being used, the partially rounded tip 38 smoothly guides the muscle from against the dilator D to the partially rounded smooth outer blade surface 40 of the retractor 20'. Therefore, after the final dilator is placed, retractor 20' can then be placed against the dilator D and slid down into position with the partially rounded tip 38 of distal end 32 smoothly guiding the muscle from against the dilator D to the partially rounded smooth outer blade surface 40 of the retractor 20'. The partially rounded tip 38 is shaped to provide a clean contact against a cylindrical dilator D and allow a clean entry for the retractor 20' without muscle interposing between the retractor 20' and the dilator D. More particularly, the partially rounded tip 38 is preferably shaped such that it provides a right angle 39 where it meets the inner surface 36 of the retractor. Thus, the partially rounded smooth outer blade surface 40 and the rounded tip 38 minimize the tendency of the retractor 20' to hang-up on tissue when placing it into a tight intermuscular or transmuscular plane.

FIG. 12 shows a cross sectional view of a dilator D cradled within the distal end 32 of retractor 20'. For one preferred example of this embodiment used in lumbar surgery, at the tip 38 of retractor 20', the width of the retractor blade is about 10 mm. The depth inside preferably measures about 7 or 8 mm from the front surface of the first face 18 to the teeth 22 located on the second face 19, which engage the articular process. As noted above, the transition from the first face 18 to the second face 19 is preferably about a 90 degree curvature or quarter of a cylinder with a preferred diameter of about 9 mm. These dimensions increase and transition to about 16 mm width and about 11 mm depth near the proximal end 31 of faces 18 and 19, respectively. Therefore, the width of the first face 18 and second face 19 both preferably increase from the distal end 32 to the proximal end 31 near the handle 12.

Referring now to FIG. 13, retractor 20" is shown, which is a further modified version of retractor 20', and which includes an optional third face 42 that is incorporated into the distal end 32 of blade 14. In accordance with embodiments of the present invention, the distal end 32 is generally U-shaped, as shown in the cross section depicted in FIG. 14. The first face 18 and second face 19 are preferably tapered, and as a result, when in use, U-shaped surfaces provide a working window of about a 5 to 10 mm opening for accessing the transverse process at a position lateral to the articular complex.

Similar to second face 19, and in accordance with embodiments of the present invention, third face 42 preferably includes at least one co-planar toothed structure 22, and more preferably, a plurality of toothed structures, such as two toothed structures, or alternatively, four toothed structures as shown in FIG. 13. The forward projecting teeth 22 serve to engage the lateral aspect of the articular complex when the retractor 20" is in use. The toothed structures 22 are preferably situated adjacent at least one co-planar indentation 24, and more preferably, a plurality of co-planar indentations 24. The toothed structures 22 and the indentations 24 are located along a lower portion of a forward projecting lateral edge 26 of the third face 42. Preferably, the forward projecting teeth 22 and the indentations 24 are present in about the distal 8 mm of the third face 42.

In accordance with embodiments of the present invention, the distal end 32 of the retractor 20" shown in FIG. 14 preferably includes about a 180 degree curvature along its interior surface 36, wherein the 180 degree curvature is, advantageously, shaped to receive a cylindrical shaped dilator so that the retractor 20" may be lowered down around the dilator, thereby displacing the tissue from around the dilator to the outer surface 40 of retractor 20". In addition, as with the curvature or quarter-rounded bend 34 between the first face 18 and the second face 19, a curved transition or quarter-rounded bend 34 is preferably used to transition between first face 18 and third face 42. The bend 34 can take the form of a constant radius curve, or when both the first face 18 and the third face 42 are tapered, the curved transition can take the form of a tapered conic section consistent with the taper of the first face 18 and the taper of the third face 42. The U-shaped three faced blade 14 allows the retractor 20" to be used from either side of the spine and still engage the articular complex cephalad to the transverse process. For one preferred example of this embodiment used in lumbar surgery, the diameter of the U-shaped blade preferably ranges between 3 to 10 mm, and more preferably the diameter is between about 6 or 7 mm at the distal end 32 of the blade 14.

Referring now to FIG. 15, in accordance with embodiments of the present invention, the distal end 32 of retractors 20, 20', or 20" can also optionally include a modified area at its tip that includes at least one terminal indentation 44. More particularly, as shown in FIG. 15, a terminal indentation 44 can be provided, wherein the terminal indentation 44 has a curved shape, and more preferably, a semi-circular shape, and wherein the terminal indentation 44 typically spans the width of the first face 18. Alternatively, as shown in FIG. 16, a terminal indentation 44 can be provided at the distal end 32, wherein the terminal indentation 44 is narrow and only occupies a portion of the width of the tip of first face 18. The terminal indentation 44 can be used to engage the distal end 32 of the retractors 20, 20', or 20" against the transverse process of a vertebra of the spine.

Referring now to FIG. 17, the distal end 32 of retractors 20, 20', or 20" can also optionally include a distal tooth, or alternatively, a plurality of distal teeth 45. The distal teeth 45 can be used to engage the transverse process of a vertebra of the spine.

Figure 18:
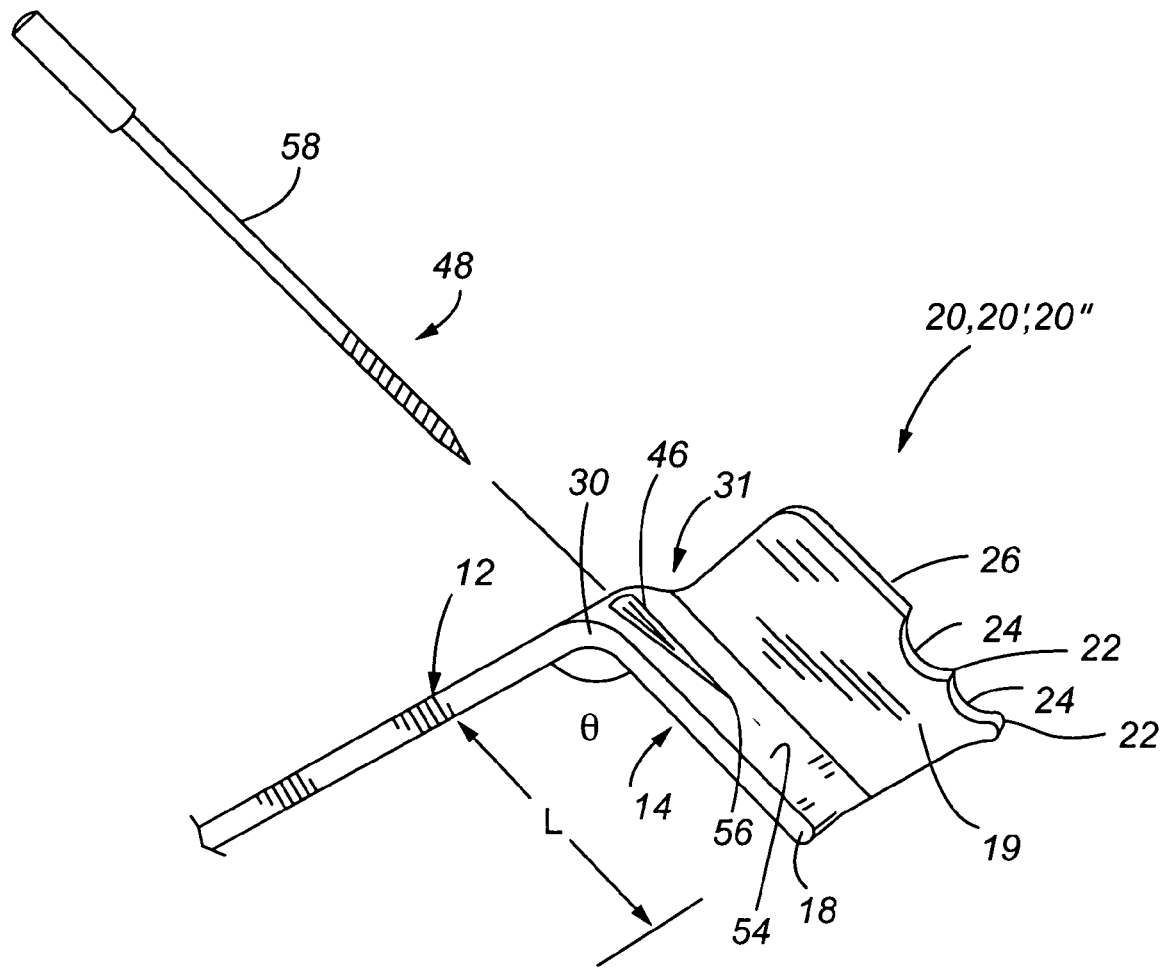
FIG. 18 is a partial perspective view of the retractor shown in FIG. 4 with a tool groove.

In accordance with embodiments of the present invention, and referring now to FIG. 18, in yet a further modification of the second embodiment of the present invention, the blade portion 14 of retractors 20, 20', or 20" can optionally include a tool groove 46. Tool groove 46 is sized to cradle a surgical tool, such as tap 48, to assist a surgeon in aligning the tap 48 with a desired target location. More particularly, tool groove 46 is an indentation or channel like feature that is formed in at least the proximal end of blade 14. Tool groove 46 may extend along only a portion of the length L of blade 14, or tool groove 46 may extend along the full length L of blade 14.

Figure 19:
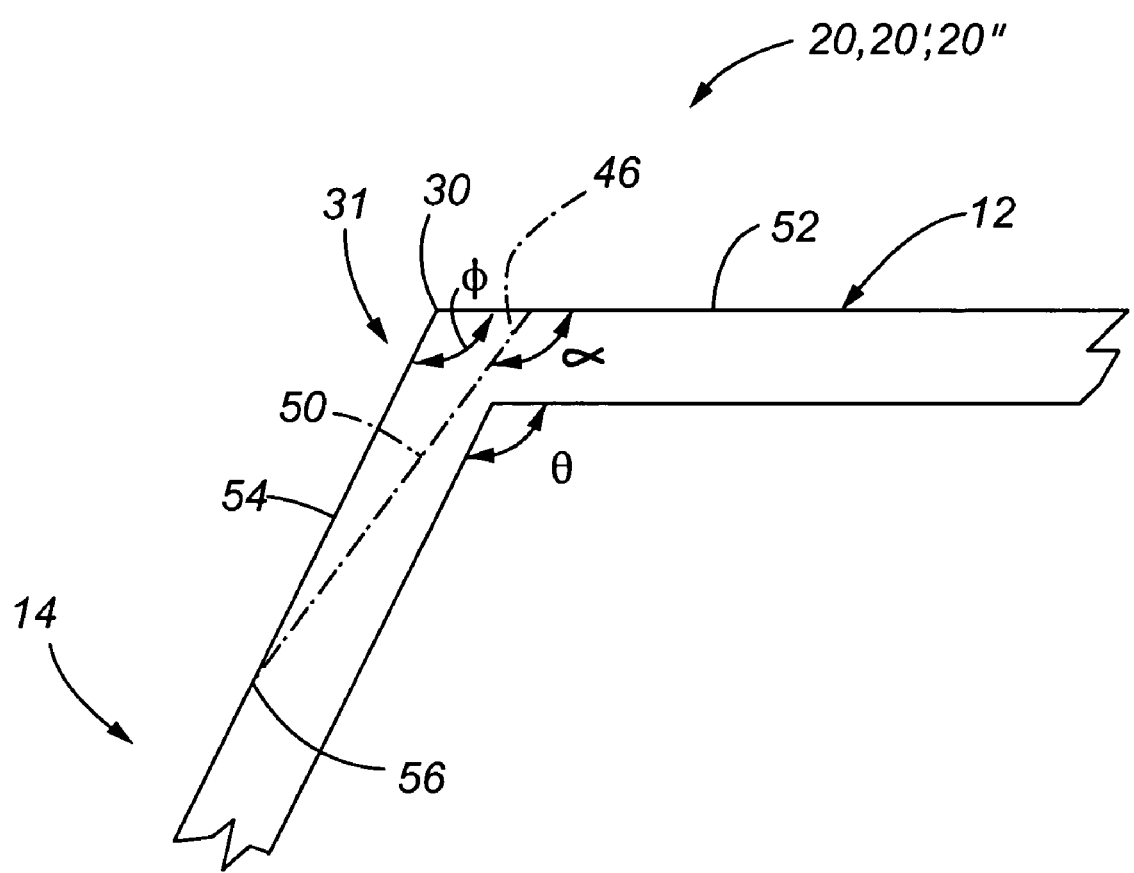
FIG. 19 is an enlarged side elevation view a retractor having a tool groove at the proximal end of the blade.

Referring now to FIG. 19, in accordance with embodiments of the present invention, an enlarged partial side elevation view of the proximal end of blade 14 is shown, including the intersection 30 between the handle 12 and the guide portion 14. For the example shown in FIG. 19, retractors 20, 20', or 20" having a partial tool groove 46 is depicted, with the tool groove 46 having a back surface 50. The back surface 50 of tool groove 46 intersects a top surface 52 of the handle 12 at an angle α. Also shown in FIG. 19 is the front surface 54 of the first face 18 of blade 14. Front surface 54 of first face 18 forms an angle φ with the top surface 52 of handle 12. Preferably, angle α is greater than angle φ, such that back surface 50 of tool groove 46 intersects the front surface 54 of first face 18 at tool groove end 56. Thus, back surface 50 of tool groove 46 serves as an inset and an alternately angled surface than that of the front surface 54 of first face 18.

Referring still to FIGS. 18 and 19, as noted, tool groove 46 may be formed in only a portion of first face 18 of blade 14, such as the upper half or upper one-third of first face 18. FIG. 18 illustrates that in one preferred embodiment, tool groove 46 tapers along a portion of the length of first face 18, where it terminates at tool groove end 56. Thus, tool groove 46 may be of a variety of depths set into the front surface 54 of first face 18. For example, tool groove 46 may be relatively shallow near handle 12, such that tool groove 46 cradles only a portion of the shaft of a tool, such as the shaft 58 of tap 48, or it may relatively deep near handle 12, such that it cradles all or nearly all of the circumference of the tool. Furthermore, as shown in FIG. 19, tool groove 46 preferably varies in depth along its length within first face 18, such that it essentially terminates at a tool groove end 56 at some point along the length of first face 18. In so doing, the back surface 50 of tool groove 46 serves as a guide plane for the shaft 58 of a surgical tool, such as tap 48. The tool groove end 56 can terminate at different locations along the length of first face 18, resulting in the possibility of separate retractors having tool grooves 46 with back surfaces 50 having different guide planes, thus yielding tool grooves 46 with back surfaces 50 having a variety of slopes or pitches.

In using retractors 20, 20', or 20" having a tool groove 46, after inserting the retractor into an incision and exposing an internal surgical site, the surgeon places the shaft 58 of a tool, such as tap 48, within tool groove 46. The tool groove 46 supports the shaft 58 of tap 48, thereby allowing the surgeon to better align the tap 48 with the patient's internal surgical site. If a tap 48 is used, the surgeon may rotate the tap 48 at the surgical site while maintaining the tap 48 in contact with the back surface 50 of tool groove 46, thereby creating a precisely aligned hole for an implant, such as a pedicle screw.

The retractors described herein are preferably made of a material that allows the handle and blade portions to be manipulated without undue amounts of deflection or deformation when used in a surgical procedure. Accordingly, the tip needs to be adequately robust to function as retractor without deforming. Materials envisioned for use in constructing the retractors include metals, plastics, and ceramics, and combinations of these materials. Preferably, the retractors are made of stainless steel.

The retractors of the present invention are used in the method as further set forth as follows. A surgical approach between the erector spinae and multifidus approaches the lateral facet and superomedial transverse process directly with no muscular detachment and avoids both the medial and lateral branches of the dorsal primary ramus and associated vessels. Orientation is appropriate for direct placement of pedicle fixation with minimal muscular retraction. Mobilization of a 4 to 5 cm midline incision allows direct bilateral exposure. Medial retraction of the multifidus after detaching its tendinous insertion to the mamillary process is simplified by stabilizing the retractor 20, 20', or 20" against the rod. Interbody fusion is accomplished via a transforaminal approach. Microsurgical technique allows for coagulation and sharp division of the inferior foraminal vein (or plexus) and retraction of foraminal fat with preservation of undisturbed perineural and epidural tissue planes to minimize potential for fibrosis. Interbody fusion is performed conventionally with bone and or synthetic devices. Use of an intradiscal spreader and securing the opening with the segmental fixation simplifies preparation of the disk space and improves restoration of lordosis with dorsal compression after grafting.

The lumbar musculature posteriorly may be considered as a medial and lateral complex. The bulk of the medial musculature is the multifidus which is supplied by the medial branch of the dorsal primary ramus of the nerve and accompanying vessels, as well as the artery related to the pars interarticularis. The bulk of the lateral musculature is the longissimus thoracis and illocostalis supplied by the intermediate and lateral branches of the dorsal ramus. Approach is the intermuscular plane along the lateral aspect of the multifidus and allows direct access to the lateral facet and superomedial transverse process in an area devoid of muscle attachment. While the medial branch traverses the lateral facet to the mamilloaccessory notch, and the intermediate and lateral branches penetrate the longissimus and iliocostalis from their ventromedial surface, approach for pedicle screw placement may be consistently accomplished without disturbing nerves or vessels.

After reflection of the thoracolumbar fascia, the erector spinae aponeurosis may be divided along the course of its fibers. Some superficial fibers of the multifidus may be seen joining the underside of the ESA. There is a tendency for the longissimus to wrap slightly over the dorsal aspect of the multifidus which may typically be well seen on the preoperative CT or MRI. As one drops down the lateral aspect of the multifidus, the tendinous insertion to the mamillary process is typically well seen with a little fat present both in the intermuscular plane and lateral to the facet. Additionally the contrasting course of the longissimus and multifidus is often seen.

In some individuals the bulk of the multifidus in the lower lumbar spine may make for a relatively oblique approach and potentially make it relatively more difficult to approach pathology in the spinal canal. In this situation, a muscle splitting approach through the multifidus may still minimize the required exposure.

Once the instrumentation is placed, exposure for the fusion is performed. Dividing the insertion of the multifidus to the mamillary process on the superior articular process of the lower vertebra allows retraction of the multifidus over the facet capsule with no further muscle detachment required. While use of a hand retractor 20, 20', or 20" may be adequate to pull the multifidus medial against the spinous process, it is preferable to retract using leverage against the rod or instrumentation. Removal of the inferior articular process and a portion of the superior articular process provides direct access to the foramen. Use of the operating microscope allows for an interbody fusion with exposure and visualization comparable to microdisectomy. Exposure of the superior aspect of the pedicle of the lower level confirms location and allows coagulation and division of the inferior foraminal vein or plexus in a safe location. If the exposure is extended cephalad in this plane, the epidural vessels and fat may be minimally disturbed and retracted preserving the epidural and perineural planes while exposing the disc. There is generally a window 10 to 12 mm in width allowing work in the disc with no retraction of neural elements. Intradiscal fusion may be accomplished conventionally with bone or prosthesis. The use of intradiscal spreaders with temporary fixation from the instrumentation allows for easier work in the disc space and subsequent compression on the graft allows restoration of lordosis. With care it is possible to bridge the foraminal space with graft for posterior facet fusion.

In most cases canal pathology may be adequately treated. One can, however, go to the midline to be sure of adequate decompression. Once the inferior articular process is removed the ligamentum flavum and hypertrophic buildup most commonly associated with degenerative stenosis and instability can generally be removed exposing the lateral dural sac, as necessary. Most central disc protrusions have been successfully removed as well as superior or inferior fragments.

Preferably, and as one of skill in the art will appreciate, an intermuscular plane of exposure provides easy access to the spine, minimizes disruption to the erector spinae and multifidus, and avoids damage to the neurovascular supply of posterior musculature. The present invention is particularly useful in performing an instrumented transforaminal interbody and facet fusion performed while detaching only the insertion of the multifidus to the mamillary process at the level of fusion. In a preferred embodiment, the retractor 10 of the present invention hooks on the lateral facet cephalad to the transverse process, retracting the longissimus laterally. In such a manner, the superomedial transverse process and lateral facet is free of muscular attachment allowing palpation of the local anatomy for pedicle screw placement.

Preferably, the screw is placed just cephalad to the accessory process avoiding any muscle detachment being required. At the caudal vertebra, the retractor may be hooked against the multifidus below the transverse process allowing visualization of the extent of fixation desired. Using the present invention, it is possible to perform an instrumented lumbar fusion comparable to that accomplished with a mid-line approach, but with much less invasive paramedian approach, requiring decreased neurovascular and muscle dissection and sparing adjacent segments.

To provide further written description and enablement support for the present invention, the following U.S. patents are incorporated in their entireties by this reference: U.S. Pat. Nos. 5,891,147; 6,270,498; 6,080,155; 6,245,072; 5,895,352 and 6,206,826.

In accordance with embodiments of the present invention, the present method and devices are useful in intermuscular foraminal facet retraction. Accordingly, in at least one embodiment, the retractor 10 is configured to have a depth ranging from between about 2 to about 10 cm and the retractor 10 has a hook or prominence 16 associated therewith so as to engage a lateral facet or muscle so as to maintain the retractor position. The retractor blade 14 is angled and has a sufficient depth to provide adequate retraction for screw placement. The engagement of the facet or deep muscle provides a mechanical advantage such that the retraction operation is made easier and the retractor 10 can be maintained in a desired position. The present invention also finds application in a transforaminal retraction where a lateral retractor engages a rod to maintain a desired position or instrumentation. Alternatively, a medial retraction is accomplished using a medial retractor that engages a rod laterally or that engages the instrumentation. The medial retractor retracts muscle medially and provides a working area medial to the rod in the range of 10 to 20 mm. The medial lateral portion engages the rod, providing mechanical advantage in pulling muscle medially and to maintain the desired position of the retractor 20, 20', or 20". In alternative embodiments, instrumentation may be engaged, such as a screw or projection from a screw, to provide similar muscle retraction.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A retractor for use in surgery of one or more vertebra of a spine, the retractor comprising:
   a handle;
   a blade interconnected to said handle at an intersection, said blade including a first face and a second face positioned transverse to said first face, said second face having an upper proximal edge spaced apart from said intersection, and said second face having a varied width, said blade further comprising a third face located transverse to said first face, wherein said first face is substantially perpendicular to said third face, and further comprising a quarter-rounded bend interconnecting said first face to said third face, wherein said third face is substantially parallel to said second face.

2. The retractor as claimed in claim 1, wherein said third face further comprises a plurality of co-planar forward projecting teeth.

3. The retractor as claimed in claim 2, wherein said third face further comprises an upper proximal edge located distally of said upper proximal edge of said second face.

4. A retractor for use in surgery of one or more vertebra of a spine, the retractor comprising:
   a handle: and
   a blade interconnected to said handle at an intersection, said blade including a first face and a second face positioned transverse to said first face, said second face having an upper proximal edge spaced apart from said intersection, and said second face having a varied width, wherein said varied width of said second face comprises a first larger width at a location positioned proximally of a second narrower width at a distal end of said second face, and wherein said first face has a varied width, and wherein said varied width of said first face comprises a first larger width at a location positioned proximally of a second narrower width at a distal end of said first face.

5. A retractor for use in surgery of one or more vertebra of a spine, the retractor comprising:
   a handle; and
   a blade interconnected to said handle at an intersection, said blade including a first face and a second face positioned transverse to said first face, said second face having an upper proximal edge spaced apart from said intersection, and said second face having a varied width, wherein said first face further comprises a tool groove, wherein said tool groove is located at a proximal end of said first face, wherein said tool groove forms an angle with a top surface of said handle that is greater than an angle formed by said blade with said handle, and wherein said tool groove occupies about one-third to one-half of the length of said first face.

6. A retractor for use in surgery of a spine having one or more vertebra, the retractor comprising:
   a handle; and
   a blade connected to said handle, the blade including a first face and a second face positioned substantially perpendicular to said first face, the second face including at least one projection for laterally engaging an articular process of a vertebra of the spine, said first face having a tapered width with a first larger width at a location positioned proximally of a second narrower width at a distal end of said first face, and said second face having a tapered width with a larger width positioned proximally of a narrower width at a distal end of said second face.

7. The retractor as claimed in claim 6, further comprising an interior surface including a curved transition between said first face and said second face, wherein said curved transition comprises a constant radius curve.

8. The retractor as claimed in claim 7, wherein said curved transition comprises a tapered conic section substantially corresponding to the taper of the first face and the taper of the second face.

9. The retractor as claimed in claim 6, further comprising a partially rounded smooth outer blade surface.

10. The retractor as claimed in claim 6, further comprising a third face located transverse to said first face, wherein said first face, said second face, and said third face form a U-shaped interior surface, wherein said third face further comprises a plurality of co-planar forward projecting teeth.

11. The retractor as claimed in claim 6, wherein said first face further comprises a tool groove, wherein said tool groove is located at a proximal end of said first face, wherein said tool groove forms an angle with a top surface of said handle that is greater than an angle formed by said blade with said handle, and wherein said tool groove occupies about one-third to one-half of the length of said first face.

12. A retractor for exposure of the bony spine for screw placement comprising:
   a handle; and
   a blade connected to said handle, the blade including a first planar surface for orienting substantially parallel to an axis of the spine, a second planar surface for orienting substantially perpendicular to the axis of the spine, and a third planar surface located substantially opposite at least a portion of said second planar surface and for orienting substantially perpendicular to the axis of the spine, a cylindrical or curved transition located between said second, said first, and said third planar surfaces wherein a U-shaped blade portion is formed, said second and third planar surfaces including a plurality of teeth pointing medially to engage an articular complex of the spine, at least said first planar surface and said second planar surfaces having tapered widths wherein a proximal end of said first and second planar surfaces is wider than a distal end of said first and second planar surfaces, the tapered first and second planar surfaces providing a working window for a transverse process lateral to the articular complex.

13. The retractor as claimed in claim 12, further comprising a terminal indentation or at least one distal tooth at the tip of the distal end of said first planar surface, said terminal indentation or at least one distal tooth adapted to engage the transverse process.

* * * * *

UNITED STATES PATENT AND TRADEMARK OFFICE
CERTIFICATE OF CORRECTION

PATENT NO. : 7,166,073 B2
APPLICATION NO. : 11/091970
DATED : January 23, 2007
INVENTOR(S) : Stephen Ritland It is certified that error appears in the above-identified patent and that said Letters Patent is hereby corrected as shown below:

Claim 4:

Column 13, line 41, delete " : " and insert -- ; -- therein.

Signed and Sealed this

Tenth Day of April, 2007

JON W. DUDAS
*Director of the United States Patent and Trademark Office*